United States Patent
Kotsos et al.

(10) Patent No.: US 8,506,885 B2
(45) Date of Patent: Aug. 13, 2013

(54) METHOD AND SYSTEM FOR INLET TEMPERATURE MONITORING FOR CENTRALIZED HEAT DISINFECTION OF DIALYSIS MACHINE INLET LINES

(75) Inventors: Michael Emmanuel Kotsos, Walnut Creek, CA (US); Fei Wang, Walnut Creek, CA (US); Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 13/474,022

(22) Filed: May 17, 2012

(65) Prior Publication Data

US 2012/0308431 A1    Dec. 6, 2012

Related U.S. Application Data

(60) Provisional application No. 61/491,951, filed on Jun. 1, 2011.

(51) Int. Cl.
*A61L 2/24* (2006.01)
*F01N 3/20* (2006.01)

(52) U.S. Cl.
USPC ............ 422/3; 210/636; 210/645; 210/646; 210/764; 210/767; 422/105

(58) Field of Classification Search
USPC ............ 210/636, 645, 646, 764, 767; 422/3, 422/105
See application file for complete search history.

(56) References Cited

U.S. PATENT DOCUMENTS

| | | | |
|---|---|---|---|
| 4,894,164 A | 1/1990 | Polaschegg | |
| 5,651,893 A | 7/1997 | Kenley et al. | |
| 6,022,512 A * | 2/2000 | Tanaka et al. | 422/292 |
| 6,153,102 A | 11/2000 | Kenley et al. | |
| 7,749,393 B2 | 7/2010 | Brugger et al. | |
| 2002/0112609 A1 | 8/2002 | Wong | |
| 2009/0012450 A1 | 1/2009 | Shah et al. | |
| 2011/0017665 A1 | 1/2011 | Updyke et al. | |

FOREIGN PATENT DOCUMENTS

| | | |
|---|---|---|
| DE | 19933223 A1 | 1/2001 |
| DE | 10111104 A1 | 10/2002 |
| DE | 10319221 A1 | 7/2004 |
| WO | 2007-148442 A1 | 12/2007 |

OTHER PUBLICATIONS

International Search Report and Written Opinion issued in corresponding International Patent Application No. PCT/US2012/038329 dated Sep. 6, 2012 (14 pages).

* cited by examiner

*Primary Examiner* — Dirk Bass
(74) *Attorney, Agent, or Firm* — Kilyk & Bowersox, P.L.L.C.

(57) ABSTRACT

A method for inlet temperature monitoring for centralized heat disinfection of dialysis machine inlet lines is described. The method can be used, for example, for a dialysis system which has a central water processing system used at a multiple patient dialysis treatment clinic or center. A central water processing system and a plurality of dialysis machines having fluid inlets are fluidly connected to a water supply loop which circulates heated water from the central water processing system to the dialysis machines and back to the central water processing system. A dialysis system for centralized heat disinfection of dialysis machine inlet lines of dialysis machines supplied with water by a central water processing system also is provided.

23 Claims, 7 Drawing Sheets

METHOD AND SYSTEM FOR INLET TEMPERATURE MONITORING FOR CENTRALIZED HEAT DISINFECTION OF DIALYSIS MACHINE INLET LINES

This application claims the benefit under 35 U.S.C. §119(e) of prior U.S. Provisional Patent Application No. 61/491,951, filed Jun. 1, 2011, which is incorporated in its entirety by reference herein.

BACKGROUND OF THE INVENTION

The present invention relates to a method for fluid inlet temperature monitoring for centralized heat disinfection of dialysis machine inlet lines supplied by a central water processing system. The present invention also relates to a dialysis system for centralized heat disinfection of dialysis machine inlet lines that includes fluid inlet temperature sensors at the fluid inlet lines of dialysis machines on a loop which is supplied from a central water processing system with heated water.

Renal dysfunction or failure and, in particular, end-stage renal disease, can cause the body to lose the ability to remove water and minerals and excrete harmful metabolites, maintain acid-base balance and control electrolyte and mineral concentrations within physiological ranges. Toxic uremic waste metabolites, including urea, creatinine, and uric acid, can accumulate in the body's tissues which can result in serious adverse health consequences if the filtration function of the kidney is not replaced. Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of supplied dialysis solution. The waste and toxins dialyze out of the blood through the semi-permeable membrane into the dialysis solution, which then can be suitably processed if reused or discarded.

Hemodialysis treatments are typically conducted at a clinic since the hemodialysis machines generally can require a continuous water source, reverse osmosis machinery, and drain lines for discarding the large volumes of water and dialysis solution used during a single treatment. Dialysis clinics also can provide dialysis treatment for multiple out-patients or in-patients at the same location. The dialysis machines can be supervised and maintained on-site by a trained clinical staff in a convenient and efficient manner. Dialysis machines need periodic cleaning and disinfection to maximize the efficiency and minimize bacterial and other microorganism levels within the system. Cleaning and disinfection can be done periodically (e.g., daily), or as needed after a long power down or after a completion of a dialysis treatment and before reuse of the same machine. Cleaning and disinfection, for example, can be done on a machine between the dialysis treatments of different patients that are received on the same machine. Disinfection may be chemical or heat based. Disinfectants are usually used in liquid form in order to be passed through the hydraulic system of the machine and discharged from the machine using a drain line. Even if a machine is routinely chemically disinfected, the manufacturer still may recommend periodic heat disinfections of the machine. This hydraulic system often includes one or more of water treatment, dialysate preparation, and extracorporeal dialysis modules, and other fluid pathways in the machine that will be reused. Heated water has been generated locally at the individual machines for heat disinfection. For example, in some hot water disinfection programs, heated water at a predetermined temperature is generated at the individual machines using an internal heater and the heated water is circulated through the hydraulic system of the dialysis machine for a predetermined amount of time, such as a circulation of water at 80° C. for one hour, or other suitable temperatures and times.

Some fluid heating and heat disinfection programs found in the patent literature for dialysis machines, for example, are directed towards closed loop systems that measure internal device temperatures locally at the machine. U.S. Pat. No. 4,894,164 (Polaschegg, Fresenius AG) shows an apparatus for treating blood in an extracorporeal circuit which has water from a supply water introduced into a dialysis solution container equipped with an electrically operated heater and associated temperature sensor, and also includes temperature sensors disposed in the arterial and venous blood paths inside the machine, wherein the temperature sensors report to a temperature regulating unit within the machine. Polaschegg does not have details on a disinfection program. U.S. Pat. No. 5,651,893 (Kenley et al.) shows disinfection of a dialysis machine that includes determining or selecting a disinfection temperature in advance which is controlled by the operation of a water heater in the machine and strategically placed thermistors in the machine which report temperatures of the water, and the circulation time is controlled by a clock in the CPU of a control module and the operation of the pumps and valves of the machine. U.S. Patent Application Publication No. 2009/0012450 A1 (Shah et al.) shows an extended use dialysis system which includes a cassette that includes in-line heater for heating fluid within the dialysis machine for disinfecting the machine and its lines. Shah et al. shows the temperature sensors may be incorporated in one or more places to control the temperature of the sterilizing water and to insure that the lines of the machine are thoroughly heated to kill bacteria or other microorganisms remaining, and the temperature sensors may include thermocouples, thermistors, or other suitable devices for detecting temperatures and reporting temperatures to the controller of the dialysis machine. U.S. Pat. No. 7,749,393 B2 (Brugger et al.) shows a batch filtration system for preparation of sterile fluid for renal replacement therapy which includes a temperature regulator, e.g., a temperature sensor combined with logic in controller, which regulates power to the heater to ensure a required temperature is maintained and not exceeded. Brugger et al. also shows the controller may simply respond to some predefined rate of temperature rise of the temperature sensor. U.S. Pat. No. 6,153,102 (Kenley et al.) shows disinfection of dead-ended lines in medical instruments which includes a step of experimentally determining an optimal dwell time by circulating water heated to a disinfection temperature $T_H$ into a fluid line, allowing it to remain in the line for a first dwell period, measuring the temperature in the fluid line, and withdrawing the fluid from the line, and repeating the steps in a specified manner. These references do not directly address disinfection of water inlet lines which externally supply the dialysis machines, which may not be reached by any local disinfection program that may be programmed to run in the individual machine.

Figure 1:
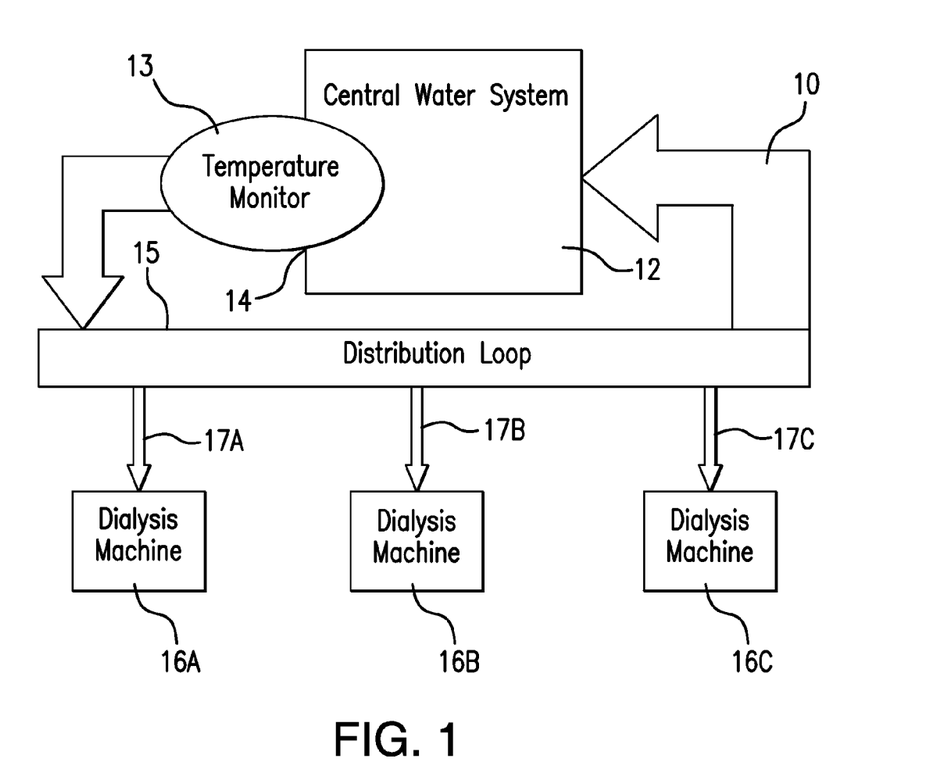
FIG. 1 shows a block diagram of a dialysis system with centralized heat disinfection which is configured for temperature monitoring at the outlet of a central water supply system which supplies heated water to fluid inlets of a plurality of dialysis machines on a shared central water fluid supply loop.

As indicated, hemodialysis treatments conducted at a clinic can require a continuous water source, among other elements. Development of some central water processing systems for some dialysis clinics has been undertaken. Referring to FIG. 1, for example, a dialysis system 10 for a clinic or other medical care facility which uses a central water supply system 12 for heat disinfection of fluid inlets to the machines is shown. The system 10 relies on a single temperature sensor 13 to monitor water temperature at the outlet 14 of the central water supply system 12. The outlet 14 is located where the central water supply system 12 directly feeds into a distribution circuit 15 (referred to as the "loop"), which supplies the heated water to all of the dialysis machines 16A-C on the loop 15. The heated water supplied in the loop 15 is available to the individual dialysis machines 16A-C via a respective fluid inlet 17A-C at each dialysis machine. The monitoring of the water temperature at the outlet of central water processing system is based on an assumption that such restricted temperature monitoring can reliably predict that water supplied to the fluid inlets of all of the dialysis machines on the loop, wherever located, will remain hot enough to provide adequate disinfection of all of the machine inlet lines connected to the loop.

As shown in FIG. 1, when the distribution loop containing the heated water is servicing several dialysis machines, the chances of having a temperature variation along the distribution loop is significant. Under the current method, having just a temperature monitor at the central water system where the heated water originates simply is not sufficient to adequately ensure that the temperature of the water is sufficient for the disinfection purposes. Under the current method, dialysis treatment centers or clinics must simply over-estimate and raise the central water system's temperature of the water to temperatures far in excess of what is needed for disinfection simply to ensure that the heated disinfection temperature of the water is achieved along the entire line of dialysis machines that are hooked to the distribution loop. This can result in significant energy costs. Further, there is always the risk that one or more dialysis machines are not receiving water having a high enough temperature for purposes of disinfection. Thus, under the current method, many assumptions are made or, out of an abundance of caution, significantly higher water temperatures are used to accommodate the temperature variation along the line. As explained below, with the present invention, significant energy savings can be achieved with the method and system of the present invention and, further, proper precautions are taken to ensure that each and every dialysis machine receives the proper temperature of water for purposes of disinfection.

The present investigators have recognized that temperature gradients may occur at fluid inlets to dialysis machines which are supplied with hot water for disinfection from a central distribution loop of a central water processing system, which may destabilize the disinfection operations and which cannot be reliably predicted by outlet monitoring alone at the central water processing system. The present investigators have further recognized that even if dialysis machines on a central water processing system have their own internal temperature monitoring and fluid heating capability, that the fluid inlet line temperatures from the loop also need to be monitored to ensure that water for inlet line disinfection is reliably available from the central water loop at a specified temperature or temperature range for that function.

The present investigators further have recognized a need to provide a temperature monitoring approach and configuration for a dialysis system which can enhance heat disinfection control and performance for fluid inlet lines of a central water processing system, even when the central distribution loop supports numerous dialysis machines on a relatively lengthy loop and/or one or more subloops are located in the same or different rooms, floors, buildings, or other different areas of the facility.

SUMMARY OF THE INVENTION

A feature of the present invention is to provide a method for inlet temperature monitoring for centralized heat disinfection of inlet lines on a plurality of dialysis machines on the same central water supply loop.

Another feature of the present invention is to provide a dialysis system having centralized heat disinfection provided for dialysis machine inlet lines of a plurality of units on the same central water supply loop.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates in part to a method for inlet temperature monitoring for centralized heat disinfection of dialysis machine inlet lines which comprises providing a central water processing system and a plurality of dialysis machines having fluid inlets which are fluidly connected to a shared water supply loop. The loop circulates heated water from the central water processing system to the fluid inlets of the dialysis machines to make heated water available for disinfection of the machines, and optionally also the internal hydraulic systems of the individual machines. Water temperatures are sensed with temperature sensors at the fluid inlets of the plurality of dialysis machines on the loop. Data on the sensed temperatures at the fluid inlets is communicated to a process controller capable of (i) comparing the sensed temperatures to a predetermined value or value range selected for disinfection, and (ii) issuing an alarm and/or controlling the temperature controller for adjusting water temperature of water at the central water processing system when a sensed inlet water temperature of a dialysis machine does not meet the predetermined value or value range. The sensing, communicating, comparing and/or issuing/controlling steps can be repeated in an iterative manner during the centralized heat disinfection of the fluid inlets.

The present invention relates in part to a dialysis system having centralized disinfection control which comprises a central water processing system having a temperature controller for loop water circulated through a fluid supply loop, a plurality of dialysis machines on the loop which have fluid inlets which comprise temperature sensors for sensing water temperatures at the fluid inlets. The fluid supply loop is capable of circulating heated water from the central water processing system to the fluid inlets of the plurality of dialysis machines and back to the central water processing system. The process controller is capable of (a) receiving data on sensed temperatures from temperature sensors at the fluid inlets of the dialysis machines, (b) comparing the sensed temperatures to a predetermined value or value range selected for disinfection, and (c) at least one of issuing an alarm and controlling the temperature controller for adjusting water temperature of water at the central water processing system when a sensed inlet water temperature of a dialysis machine does not meet the predetermined value or value range. The dialysis system further can be capable of performing the sensing, communicating, comparing and issuing/controlling functions in an iterative manner during a centralized heat disinfection of the dialysis machine inlet lines.

It is to be understood that both the foregoing general description and the following detailed description are exemplary and explanatory only and are only intended to provide a further explanation of the present invention, as claimed.

The accompanying drawings, which are incorporated in and constitute a part of this application, illustrate at least some of the features of the present invention and together with the description, serve to explain the principles of the present invention. The drawings are not necessarily drawn to scale. Like numerals in the drawings refer to like elements in the various views.

DETAILED DESCRIPTION OF THE PRESENT INVENTION

The present invention relates to a method and system for inlet temperature monitoring for centralized heat disinfection of dialysis machine inlet lines. The centralized heat disinfection can be provided in a dialysis system having a central water processing system and a plurality of dialysis machines (e.g., two, three, four, ten, twenty, thirty, fifty, or more machines) on a common water distribution circuit or loop, which are supplied with heated water by the central water processing system for disinfection of fluid inlet lines of the dialysis machines. The dialysis system provides temperature monitoring at each of the dialysis machine fluid inlet lines with real time or otherwise rapid temperature sensing and reporting of data on the sensed temperatures to a process controller. The process controller can rapidly evaluate the temperature data and issue an alert and/or make appropriate temperature and/or flow adjustments in the central water processing system if a fluid inlet temperature is found to be non-compliant with preselected values or a value range for disinfection. Depending on the temperature of the water supplied at the dialysis machine fluid inlets for their disinfection, the heated water supplied from the central water processing system also can be used, for example, in conjunction with a machine's local heater. Some dialysis machines have internal heaters, for instance, for purposes of heating dialysis fluids to body temperature or about that temperature. This integration of an external disinfection program with a heater within the dialysis machine can reduce requirements for heating or reheating of inlet water, and can avoid undesirable water vaporization or steam, which can result in energy cost savings for the clinic.

As used herein, the term "disinfect" or variants thereof refers to providing detectible/measurable control of at least one microorganism on, in, or at a component, part, surface, material, or system under disinfection treatment. "Control" refers to reducing an existing level of at least one microorganism, or preventing the growth of at least one microorganism, or preventing the emergence of at least one microorganism, or any combinations of these. As an option, the disinfection can control the presence of at least one selected or target microorganism to a count level below a predetermined or specified maximum value. Different microorganisms may have different specifications applied to them for disinfection.

The present invention includes the following aspects/embodiments/features in any order and/or in any combination:

1. The present invention relates to a method for centralized heat disinfection control for a dialysis system, comprising:

providing a central water processing system, a plurality of dialysis machines having fluid inlets which are fluidly connected to a shared water supply loop which circulates heated water from the central water processing system to the dialysis machines;

supplying heated water to the shared water supply loop from the central water processing system;

sensing water temperature with temperature sensors at the fluid inlets of the plurality of dialysis machines on the loop; and communicating data on the sensed temperature at each fluid inlet of the machines to a process controller capable of (i) comparing the sensed temperature to a predetermined value or value range selected for disinfection, and (ii) issuing an alarm and/or controlling the temperature controller for adjusting water temperature of water at the central water processing system when a sensed inlet water temperature of a dialysis machine does not meet the predetermined value or value range.

2. The method of any preceding or following embodiment/feature/aspect, wherein the sensing, communicating, comparing and issuing/controlling steps can be repeated in an iterative manner during the centralized heat disinfection of the fluid inlets.

3. The method of any preceding or following embodiment/feature/aspect, wherein the adjusting of the water temperature comprises increasing the water temperature of water at the central water processing system relative to the sensed water temperature at the fluid inlet of the dialysis machine which raised the alarm when a sensed inlet water temperature of a dialysis machine is below the predetermined value or value range.

4. The method of any preceding or following embodiment/feature/aspect, further comprising issuing an alarm comprising an audible alarm and/or an optical alarm when a sensed inlet water temperature of a dialysis machine is either above or below the predetermined value or value range.

5. The method of any preceding or following embodiment/feature/aspect, further comprising conducting of diagnostics on the fluid inlet of a dialysis machine by the process controller and/or temperature controller on the dialysis machine which raised the alarm.

6. The method of any preceding or following embodiment/feature/aspect, wherein the predetermined value or value range selected for disinfection is a minimum temperature of greater than 85° C.

7. The method of any preceding or following embodiment/feature/aspect, wherein the predetermined value or value range selected for disinfection is a temperature of greater than 85° C. and less than 100° C.

8. The method of any preceding or following embodiment/feature/aspect, wherein the process controller comprises an automatic programmable controller.

9. The method of any preceding or following embodiment/feature/aspect, wherein the temperature controller is controllable by the process controller.

10. The method of any preceding or following embodiment/feature/aspect, wherein the temperature controller comprises a manual controller controllable by a human operator.

11. The method of any preceding or following embodiment/feature/aspect, wherein the loop comprises at least one subloop having at least one dialysis machine thereon.

12. The method of any preceding or following embodiment/feature/aspect, wherein the temperature sensors are located inside housings of the dialysis machines where the fluid inlets make a connection with the machines.

13. The method of any preceding or following embodiment/feature/aspect, further comprising integrating the inlet temperature monitoring and process control with a local disinfection or heating program conducted at one or more of the dialysis machines.

14. A dialysis system with centralized heat disinfection control, comprising:
a central water processing system comprising a water heater controlled by a temperature controller;
a fluid supply loop circulates heated water from the central water processing system to a plurality of dialysis machines;
the plurality of dialysis machines having fluid inlets which are fluidly connected to the fluid supply loop, wherein the fluid inlets comprise temperature sensors for sensing water temperature supplied from the fluid supply loop to the fluid inlets; and
a process controller capable of (a) receiving data on sensed temperatures from the temperature sensors at the fluid inlets of the dialysis machines, (b) comparing the sensed temperatures to a predetermined value or value range selected for disinfection, and (c) issuing an alarm and/or controlling the temperature controller for adjusting water temperature of water at the central water processing system when a sensed inlet water temperature of a dialysis machine does not meet the predetermined value or value range.

15. The system of any preceding or following embodiment/feature/aspect, wherein the dialysis system further is capable of performing sensing, communicating, comparing and issuing/controlling functions in an iterative manner during a centralized heat disinfection of the dialysis machine inlet lines.

16. The system of any preceding or following embodiment/feature/aspect, wherein the process controller comprises a programmable central processing unit (CPU).

17. The system of any preceding or following embodiment/feature/aspect, further comprising a wired or wireless communication system providing data transfer and control communications between the process controller and the dialysis machines, and control communications between the process controller and the temperature controller of the central water processing system.

18. The system of any preceding or following embodiment/feature/aspect, wherein the communication system comprises an ethernet connection.

19. The system of any preceding or following embodiment/feature/aspect, wherein the loop comprises at least one subloop having at least one dialysis machine thereon.

20. The system of any preceding or following embodiment/feature/aspect, wherein the temperature sensors are located inside housings of the dialysis machines where the fluid inlets make a connection with the machines.

21. The system of any preceding or following embodiment/feature/aspect, wherein each dialyzer machine further comprises a functional processor board in bidirectional communication with the process controller 22. The system of any preceding or following embodiment/feature/aspect, wherein central water processing system further comprises a pump unit for moving the heated water through the loop.

23. The system of any preceding or following embodiment/feature/aspect, further comprising an integration of the inlet temperature monitoring and process control with a local disinfection program conducted at one or more of the dialysis machines.

The present invention can include any combination of these various features or embodiments above and/or below as set forth in sentences and/or paragraphs. Any combination of disclosed features herein is considered part of the present invention and no limitation is intended with respect to combinable features.

Figure 2:
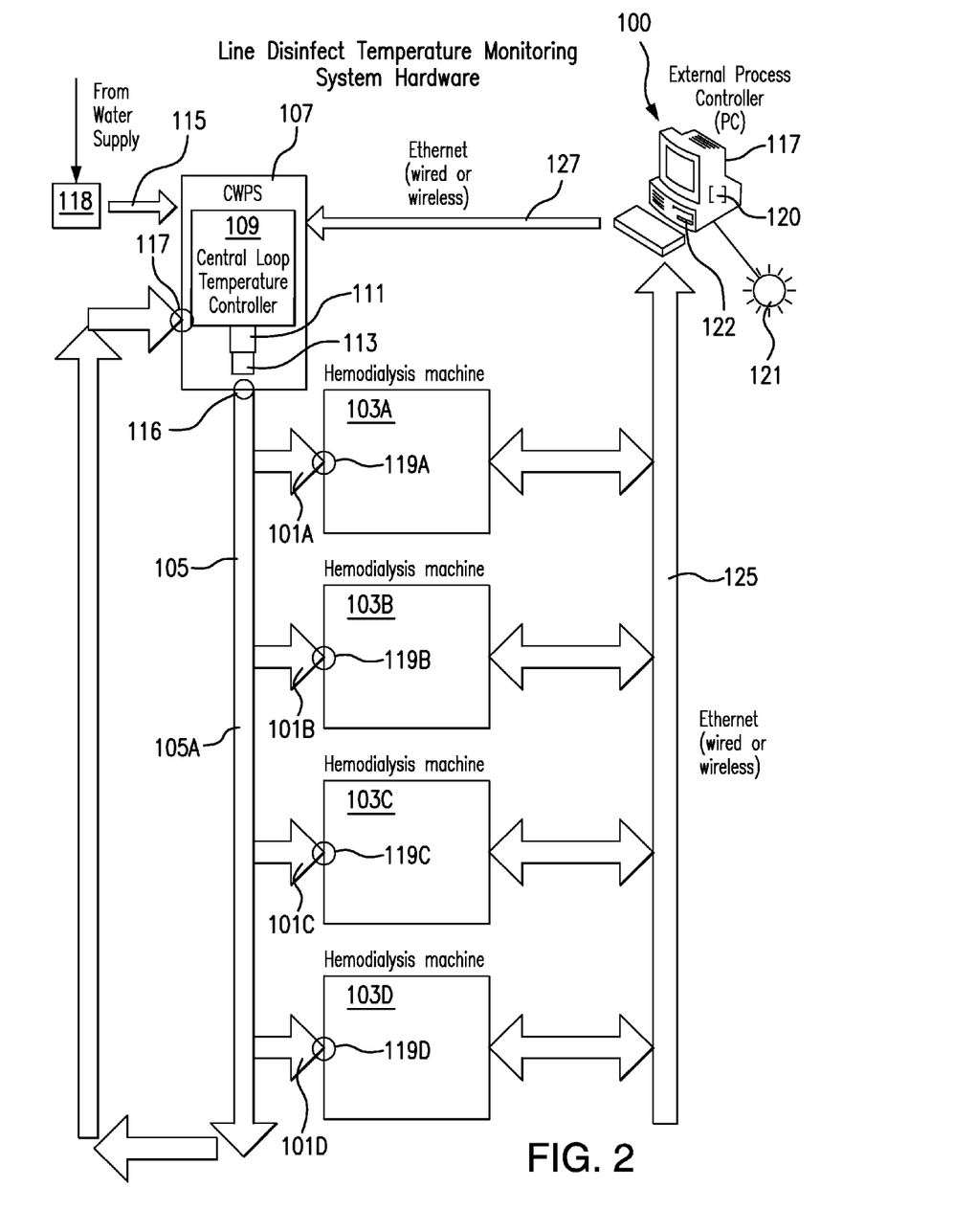
FIG. 2 shows a block/schematic diagram of a dialysis system configured for inlet temperature monitoring for centralized heat disinfection of dialysis machine inlet lines of a plurality of dialysis machines on a shared central fluid supply loop, according to an example of the present invention.

With regard to the present centralized disinfection method and system, temperature gradients can be reduced or eliminated in heated water supplied on demand for disinfection at fluid inlets of dialysis machines on a loop of a central water processing system. As shown in FIG. 2, for example, a dialysis system 100 having centralized heat disinfection is configured for inlet temperature monitoring at a plurality of separate dialysis machine inlet lines 101A-D associated with a plurality of dialysis machines 103A-D, respectively, on a shared disinfectant fluid supply loop 105. Loop 105 is the same as the primary 105A in this example. Although four dialysis machines are shown for this example, it will be appreciated that the number of dialysis machines is not limited thereto. Although it may be any number of 1 or greater, it generally will include a plurality of machines (i.e., two or more) from a practical standpoint when the system is used in a clinical setting. Heated water is supplied and circulated through the loop 105 by central water processing system 107 ("CWPS"). The central water processing system 107 is equipped, in this example, with a temperature controller 109, a water heater 111, and a pump device 113. The central water processing system 107 further can include, for example, water cleaning and filtering treatment subsystems or can be integrated with such subsystems (118), which can include systems conventional in the industry for those functions which are adapted for this system. These other possible subsystems of the central water processing system may not be fully shown here in order to focus the example on the centralized heat disinfection function of the system. The central water processing system 107 can include a continuous fluid pathway through these devices such that water flow can continuously emerge from the outlet 116, flow through loop 105, and re-enter the system 107 at an inlet 117. The water heater 111 can adjust the temperature of water passing through the central water processing system 107 under the control of temperature controller 109. The controlled heating of water in the central water processing system 107 can be performed in any suitable manner. Water heating in system 107 can be performed, for example, as an in-line process, or by using a temporary dwell vessel or chamber inside the unit into which water is fed and discharged at similar rates while water is temporarily accumulated and held during heating for a finite residence time in the vessel, e.g., a heat exchanger or a heated fluid container arrangement such as shown in U.S. Pat. No. 4,894,164, which is incorporated herein by reference in its entirety. The pump device 113 can control the water movement and flow rate of water through loop 105. The type of water pumping device is not necessarily limited. As one option, the pumping device can be one which can provide a flow rate in the central loop 105 adequate to maintain a linear (laminar) flow velocity, such as greater than about 3 feet/second, or greater than about 4 feet/second, or greater than about 5 feet/second, or other rates. As an option, each machine along the loop can draw up to about 1 liter/min during rinse modes, for example, from about 0.1 to about 1 liter/min, or from about 0.2 to about 0.9 liter/min, or from about 0.3 about 0.8 liter/min, or from about 0.4 to about 0.75 liter/min, or other values. Assuming an average clinic has 20-30 machines hooked up, for example, that could result in a central loop demand of up to 30 liters per minute. A water supply system of the present invention can include the line disinfect temperature monitoring capability shown herein to meet the desired overall water demands of the system, including the central loop demand. The operator can modify the loop parameters based upon the reported machine inlet temperatures. The line pressure within loop 105 can be kept constant or substantially constant value in all of the fluid lines of loop 105. The type of tubing is not limited as long as it is watertight and tolerant of the temperatures of the heated water that is circulated through the loop lines. The tubing can be, for example, heat tolerant synthetic resin, metal, or other watertight materials which can be formed into tubing or other elongated closed-wall conduit structures. As an option, the tubing can have insulation to minimize energy losses from the tubing along the loop. The tubing insulation can be, for example, external thermal insulation material, such as jackets, cladding, wrappings, coatings, and/or other forms of thermal insulation suitable for tubing, that can cover, surround, and/or encase substantial external surface area of the tubing to reduce heat losses from the tubing. The tubing insulation material is not necessarily limited, and can be, for example, elastomeric foam (e.g., foam tubes or jackets), PVC, fiberglass cloth, silicone cloth, or other thermal insulation materials, individually or in any combinations thereof. The tubing may be flexible or stiff. The water inlet lines 101A-D can connect the primary loop 105A of central loop 105 to the hydraulic system inlet ports (not shown in this view) of the dialysis machines, for example, as tap lines optionally fitted with one-way directional valves (e.g., backflow preventer valves) which can permit flow only towards inlet ports on the dialysis machines. As an option, the loop can be built into the walls and/or ceilings of a clinic or other facility where the dialysis machines are housed. At each machine location, there can be, for example, a wall valve that allows a hose (e.g., flexible hose) to be attached to the machine inlet.

The water line 115 can supply water to the central water processing system 107, which is used in loop 105 and the dialysis machines. The water supplied by line 115 can meet similar requirements as process and rinse water used in conventional dialysis machines. For example, the water used in loop 105 can be selected or pretreated to meet the AAMI standards for water for hemodialysis (e.g., RD62:2006). The water supplied via line 115 can be supplied, for example, to loop 105 from a water (pre)treatment module 118, which can provide prefiltered and cleaned water. Water (pre)treatment modules which can be used for this purpose are not necessarily limited, and can include adaptations in scale, of conventional water treatment modules used on tap water before supplied to an individual hemodialysis machine, such as disclosed, for example, in U.S. Pat. No. 5,651,893, which is incorporated in its entirety by reference herein. The water line 115 can introduce water into the central water processing system 107 as needed, such as a volume sufficient to fill fluid pathways in the central water processing system 107 and loop 105, or as make-up water to replenish any amounts drawn by the dialysis machines or otherwise removed/lost from the loop 105 during use. Manual or automated valving control (not shown) can be used for this function. The dialysis machines 103A-D on loop 105 can be any hemodialysis machine which can be adapted for use in the present systems as disclosed herein, such as including the fluid inlet and process control adaptations. As an option, a dialysis machine which can be adapted for use in the present dialysis system and method can be a 2008 series Hemodialysis Machine ("2008 machine"), manufactured by Fresenius Medical Care AG & Co. KGaA, Bad Homburg, Germany. As an option, one specific 2008 machine which can be adapted for use is the 2008K$^2$ Hemodialysis Machine.

A process controller 117 included in dialysis system 100 is capable of receiving data on sensed temperatures from temperature sensors 119A-D at the fluid inlets 101A-D of the dialysis machines 103A-D. The temperature sensors 119A-D can be, for example, thermistors (for example, NTC or PTC thermistors), thermocouples, or resistors (for example, platinum resistors having a nominal resistance of about 100 ohm at 0° C.). The process controller 117 can comprise at least one processing unit 120, such as a central processor unit (CPU), which is programmable to execute instructions and run one or more programs on data received from the temperature sensors 119A-D and take responsive action, if necessary and such as dictated by a program running on the processing unit 120, at the temperature controller 109 of the central water processing system 107. For example, the processing unit 120 can be programmable to compare the temperatures sensed by sensors 119A-D at the fluid inlets 101A-D of the dialysis machines to a predetermined value or value range selected for disinfection. As an option, when any sensed inlet water temperature of a dialysis machine does not meet a predetermined value or value range, the process controller 117 can command an alarm device 121 to issue an alarm, or send a control command to the temperature controller 109 to adjust water temperature of water at the central water processing system 107, or both. The detection of the non-compliant inlet temperature at a dialysis machine can be responded to manually or automatically. The alarm 121 can be, for example, an acoustic or audible alarm, an optical alarm (e.g., a flashing warning light or display on a computer screen, or other visual cues), or combinations of alarms, which can obtain the attention of a human technician or operator. As one option, the technician may take steps to resolve the non-compliance, such as by checking the non-compliant line for possible mechanical problems, or manually changing the temperature setting at the temperature controller 109 to increase the loop temperature if the detected temperature at a machine inlet was below the selected limit value, or increase the flow rate of the fluid in the central loop 105 such as by increasing the pumping rate at the pump used by the central water processing system, or combinations of these.

In selecting the loop water temperature which is suitable for disinfection at least at the fluid inlet lines of dialysis machines, the predetermined value or value range selected for disinfection can be, for example, a minimum temperature of greater than about 85° C., or a temperature range of greater than 85° C. and less than 100° C., or from greater than 85° C. to 95° C., or from greater than 85° C. to 90° C., or from 86° C. to 99° C., or from 87° C. to 95° C., or other suitable temperature ranges for disinfection. A relatively lower temperature value for disinfection may require longer application times than a higher temperature to provide the same amount of disinfection. It also can be desirable to avoid vaporization and steaming of water in the fluid lines. Steaming may cause, for example, non-uniform heating of the fluid inlet lines and hydraulic systems being disinfected, vapor lock, or cause other issues. In view of this consideration, as one option, the temperature value or range that is selected for the loop water that is delivered to the dialysis machine inlets has an upper limit less than the boiling point of water. The type of microorganism(s) targeted by the centralized disinfection also can be a factor in the selection of the temperature limits.

As indicated, as an option, the process controller 117 can be used to automatically send a control command to the temperature controller 109 to adjust the water temperature of water at the central water processing system 107 when a non-compliant temperature is detected at one or more of the sensors 119A-D at the fluid inlets of the dialysis machines. As indicated, to provide this action, temperature controller 109 can control water heater 111 in the central water processing system 107. Data or control communications between sensors 119A-D and process controller 117, and between the process controller 117 and the temperature controller 109 at the central water processing system 107, can be made through wired or wireless connections 125 and 127, respectively. Signal transmission rates for both operations can be set for high frequencies (rates) for providing continuous or essentially continuous real-time process control. Periodic, semi-continuous, or intermittent temperature sensor signal transmission to the process controller 117 and control signaling from the process controller 117 to the temperature controller 109 also may be used where temperature gradients at the dialysis fluid inlets are adequately prevented. Wired connections can include, for example, wired Ethernet, LAN, Internet, bus, and/or other direct wire connections. A wired data connection of the process controller 117 to the temperature sensors 119A-D can be direct or through a functional processor board on-board the dialysis machine, such as detailed further in a later figure. Wireless connections can include, for example, radio frequency (RF), infrared, wireless Internet, and/or other wireless communications and protocols. Wireless data communications can be transmitted directly from the temperature sensors 119A-D, if equipped for that functionality, to a suitable receiver on-board the process controller 117 or in communication therewith, or via a separate transmitter controlled by the indicated functional processor board on-board the dialysis machine, or using other suitable modes of wireless signal transmission. The communications between the controller 117 and the temperature controller 109 and the sensors 119A-D can comprise connections over a local area network (LAN) (e.g., an Ethernet, LAN, or a wide area network (WAN) (e.g., the Internet)). The programs run on processing unit 120 of process controller 117 and optionally can be stored on computer readable media 122. The computer readable media 122 can comprise any available media that can be accessed by the processing unit 120. For example, computer readable media 122 can comprise computer storage media. Computer storage media can include, for example, any one or more of volatile and/or nonvolatile memory and removable and/or non-removable media implemented in any method or technology for storage of information, such as computer readable instructions, data structures, program modules, or other data. Examples of such computer storage media includes, but is not limited to, RAM, ROM, solid state disks, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the processing unit 120.

Figure 3:
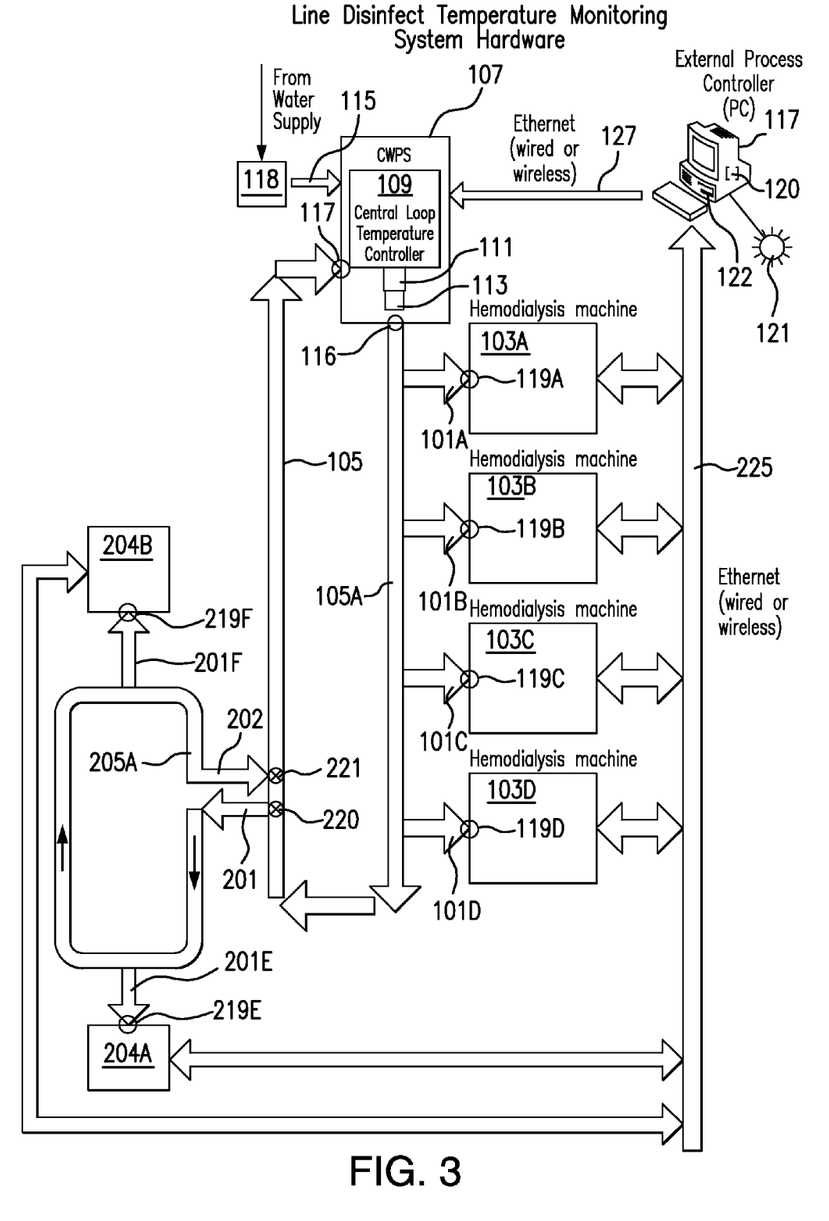
FIG. 3 shows a block/schematic diagram of a dialysis system for inlet temperature monitoring for centralized heat disinfection of dialysis machine inlet lines of a plurality of dialysis machines on a central fluid supply loop including a primary loop and at least one subloop, according to an example of the present invention.

Temperature gradients can be reduced or avoided in more complicated loop layouts for central water processing systems for centralized disinfection, such as where the distribution loops support numerous machines on a relatively lengthy loop and/or one or more subloops are located in different rooms, locations, floors, and so forth, of the treatment facility. As shown in FIG. 3, for example, a dialysis system 200 for inlet temperature monitoring for centralized heat disinfection of dialysis machine inlet lines of a plurality of dialysis machines on a fluid supply loop including a primary loop 105A and a subloop 205A. Subloop 205A can be fed water from the central loop 105A via diversion of water into tap line 201, such by using a multi-directional valve 220. In this example, subloop 205A supplies heated water to two additional dialysis machines 204A and 204B via inlet lines 201E and 201F before circulating the water from subloop 205A back into primary loop 105A via connection 202, which can be another multi-directional valve 221. Inlet temperature sensors 219E and 219F of the dialysis machines 204A and 204B can operate similarly as indicated for sensors 119A-D. The data communication line 225 can operate similarly as data connection 125 described with respect to in FIG. 1, other than including data from additional sensors 219E-F on the machines 204A-B on the subloop 205A. Although only a single subloop 205A is illustrated in the example of FIG. 3, more than one, e.g., two, three, four, or more subloops may be branched off the primary loop 105A. All of the loops can be supported by the same central water processing system 107. Pumping capacity at the central water processing system can be adjusted to accommodate the additional fluid lines of the subloop or subloops.

Figure 4:
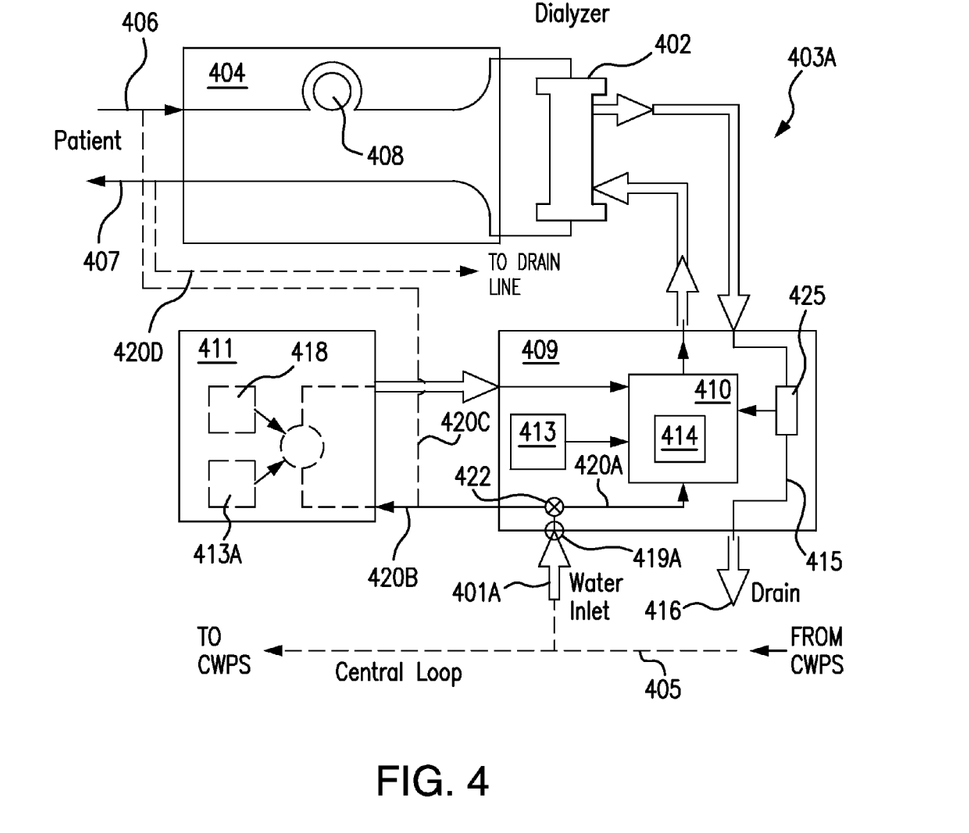
FIG. 4 shows a block diagram in an enlarged view of a portion of the dialysis system of FIG. 2, according to an example of the present invention.

As shown in FIG. 4, a hemodialysis machine 403A is illustrated in more detail which has heated water for disinfection made available from a central loop 405 via water inlet 401A with temperature sensing at the inlet by temperature sensor 419A. Dialysis machine 403A can be representative of machine 103A, or any of the other machines 103B-D and 204A-B on central loop 105 of a central water processing system 107 such as shown FIGS. 2 and 3. Other dialysis machines along the same central loop 405 can have similar configurations as machine 403A. Water inlet 401A can receive disinfection water from the central loop 405 of the central water processing system ("CWPS"), and conducts the water into the hydraulic systems of the machine. The dialysis machine 403A, in this example, has a blood flow circuit 404, through which blood passes from a patient to a dialyzer 402, and through which treated blood returns to the patient (not shown) via arterial and venous lines 406 and 407, respectively. The dialyzer can be a small disposable device having a semi-permeable membrane. The membrane allows wastes, electrolytes, and water to cross but restricts the passage of large molecular weight proteins and blood cells. Blood is pumped across one side of the membrane as dialysate is pumped in the opposite direction across the other side of the membrane. The dialysate is highly purified water with salts and electrolytes added. The dialyzer 402 can have any conventional design, for example, such as a hollow fiber membrane construction. A dialyzer can consist, for example, of a bundle of thousands of semipermeable hollow fiber membranes through the interior of which the blood is passed, and dialysis fluid or dialysate can be circulated on the outside of the hollow fibers so that the substances to be removed from the blood enter this fluid by diffusion and/or convection. At least some portion of spent dialysis solution discharged from the dialyzer 402 can be passed through a sorbent cartridge 425, and recycled dialysis solution exiting the sorbent cartridge 425 can be combined with fresh dialysate solution in or supplied from dialysis solution container 410. The sorbent cartridge 425 can have a conventional design, for example, such as disclosed in U.S. Patent Application Publication No. 2011/0017665 A1, which is incorporated by reference in its entirety. A blood pump 408 and other conventional components can be included and used in blood flow circuit 404. A dialysate circuit 409 can store fresh dialysate and/or recycled spent dialysis fluid received from sorbent cartridge 425 before the dialysate solution is conducted to and passes through the dialyzer 402. A dialysis solution container 410 in dialysate circuit 409 can be supplied with treated water, for example, as received from a water treatment module 411, and dialysate concentrate from mixer/supply 413 (or 413A) located in at least one of the dialysate circuit 409 or the water treatment module 411. A heater 414 can be used to heat dialysate in the container 410 to body temperature (e.g., about 37° C.). The water treatment module 411 further can be used, for example, to provide temperature control on water fed from the central loop 405 into the machine before its use as process water for dialysate solution preparations, or provide some premixing of dialysate ingredients with the water with optional mixer/supply 413A, or both, before the treated water is transmitted to the dialysate solution container 410 in dialysate circuit 409. A control valve 422 located in the dialysate module 409 can be used to control movement of the water received from the loop 405 and through inlet 401A into the machine 403A, and which hydraulic flow paths the received water is initially directed into once inside the dialysis machine. Water received in water treatment module 411 from water inlet 401A may be blended with water stored or received from another source on-board the machine in a vessel 418, to adjust the water temperature to body temperature. Used dialysate and disinfectant water can be passed out of the system 403A as waste via drain line 415 which feeds a drain 416 outside the machine.

After completing a dialysis session on a patient or after a long down time or other reason, the hydraulic pathways within the dialysis machine 403A can be cleaned and rinsed before commencing a disinfection program which can include use of heated water supplied by the central loop 405 and central water processing system. Cleaning and rinsing can be performed in a conventional manner or other suitable way on a dialysis machine on the loop. Before starting the disinfection program, process fluids, such as dialysate and patient blood, usually are previously pumped out and removed from the hydraulic pathways of respective circuits and modules of the machine which came into contact with them during a treatment session. When the machine is offline (from a patient treatment standpoint) and ready for a local disinfection program, heated water received at water inlet 401A that is sensed to have a temperature which also is suitable for internal machine disinfection can be conducted to one or more, or all, of the dialysate solution container 410, the water treatment module 411, and the blood circuit 404, or any other hydraulic modules of the machine. The heated water introduced through inlet 401A can flow and circulate through the machine's internal and external hydraulic pathways before it is drained from the machine. For example, a branch conduit line 420A off water inlet 401A can feed the heated water to dialysate solution container 410, which from there can flow through the dialyzer 402 and back out via drain line 415. As indicated drainage of disinfectant water from the machine after it has circulated through the hydraulic system can be accomplished via drain line 415 feeding drain 416. Another branch conduit 420B off water inlet 401A can supply the disinfectant water to water treatment module 411, which passes back into the dialysis solution container 410, from which it can be drained after passing through the dialyzer 402 as previously indicated. Another branch conduit 420C, shown in dashed lines, can be connectible with blood flow circuit 404, such as at an entry line 406, and the disinfection water can pass through the hydraulic pathways of blood circuit 404 via dialyzer 402 and exit via a discharge line, such as line 407, from which the heated water is fed through conduit line 420D which is fluidly connected into to drain line 415 (not shown). A variety of other components apart from the disinfection system which can be used in the dialysis machine 403A are not shown to simplify the illustration, which will be appreciated and applicable by persons of skill in the industry.

Figure 5:
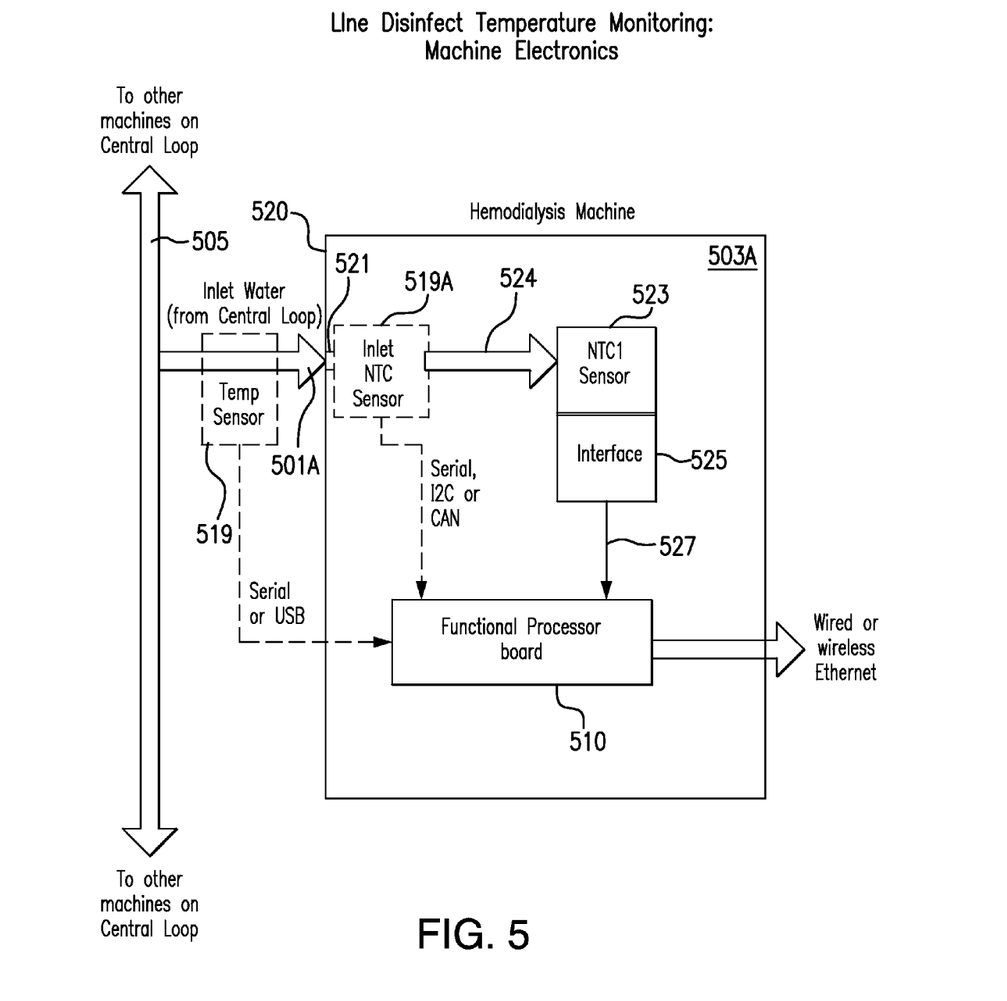
FIG. 5 shows a block diagram in an enlarged view of a portion of the dialysis system of FIG. 2, according to an example of the present invention.

The temperature sensors used to monitor temperatures at the fluid inlets of the dialysis machines can be positioned internally or externally with respect to a housing of the machine where the fluid inlet line connects with an inlet port of the machine. As shown in FIG. 5, as an option, the location of the inlet temperature sensor 519A can be inside the housing 520 of the dialysis machine 503A where the inlet line 501A from the central loop 505 connects with an inlet port 521 of the machine 503A. The internally located temperature sensor 519A can transmit sensed temperature data, for example, by an electrical connection, such as a bus connection, to a functional processor board 505. The bus connection, if used as the form of data connection, can be, for example, a serial, I2C or CAN bus, or other suitable data connection. The functional processor board 510 can relay the signals to the overall system process controller (117) via the wired or wireless data connection (125) such as shown in FIG. 2. As an option, sensor NTC1 523 can be used to measure the inlet water temperature pre-dialyzer machine. In the context of heat disinfection, for example, sensor NTC1 523 can monitor the temperature of inlet water provided by the central loop. Sensor NTC1 523 can have, for example, a Negative Temperature Coefficent sensing element mounted in the fluid path, such as a sensor 519 in inlet line 501A. Signals based on the sensed inlet water temperature can be transmitted from sensor 519 or other external sensing component to sensor NTC1 523 via wire or wirelessly 524. Sensed "Interface" 525 refers, for example, to an analog electronics circuit, such as a analog to digital signal converter, which can convert a small analog signal from sensor NTC1 523 to a digital value 527 that is monitored by the Functional Processor board 510. As shown in such options, the inlet water temperature sensors can be operable to output analog signals based on the sensed inlet water temperatures. As indicated, an analog to digital signal processor, such as interface 525, can be used, for example, to convert the analog signals outputted by the temperature sensors to digital signals for processing by the monitoring system. The analog to digital signal processor, if used, alternatively can be integrated with the temperature sensors themselves, or with the Functional Processor board, or used in other configurations providing a similar function. As another option, the inlet temperature sensor for the fluid inlet can be located outside the housing 520 on the inlet line 501A, as shown as sensor 519, and can directly send signals on sensed water temperature in inlet line 501A to the Functional Processor board 510 for processing and monitoring. The externally located temperature sensor 519 can transmit sensed temperature data, for example, by an electrical connection made to the functional processor board 510, such as by a serial bus or universal serial bus (USB), or other suitable data connection. Dialysis machine 503A can be representative of machine 103A, or any of the other machines 103B-D and 204A-B on central loop 105 of a central water processing system 107 such as shown FIGS. 2 and 3. Other dialysis machines along the same central loop 505 can have similar configurations as machine 503A.

Figure 6:
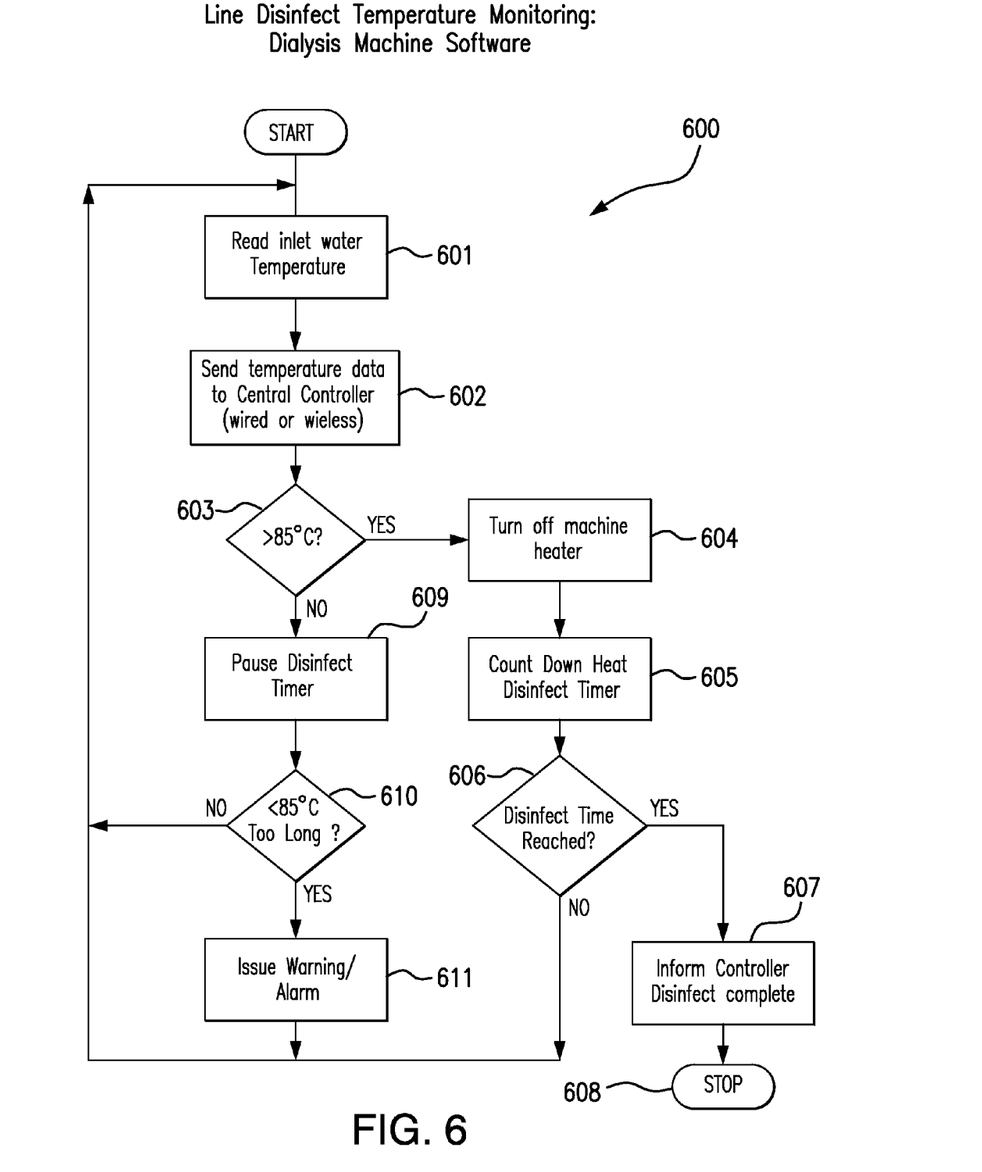
FIG. 6 shows a process flow chart of programming logic of a line disinfect temperature monitoring system which is integrated with dialysis machine software, according to an example of the present invention.

As shown in FIG. 6, as an option, a disinfection program conducted on a dialysis machine of the present method and system can be coordinated with the temperature sensing activity being done at its fluid inlet on the heated water supplied from the central loop as an integrated process 600. In this process, for example, if the temperature sensed at the water inlet of the machine exceeds 85° C. (or other temperature) to meet the selected range value criterion for this disinfection (i.e., steps 601-603), then the dialysis machine heater can be turned off (i.e., 604) as the loop water supplied has a temperature suitable for disinfection of the internal hydraulic system of the machine. In that event, if the heat disinfect timer is then reached, the controller can be informed whether the disinfect program for the machine is complete (i.e., steps 605-608), and if not the process is repeated. If the sensed temperature at the inlet is not greater than 85° C. (or other temperature) (i.e., step 603), the disinfect timer on the machine is paused (i.e., step 609), and if it still remains below 85° C. (or other temperature) for too long (based on selected wait period before rechecking it), then an alarm and/or warning can be issued to the operator (i.e., step 611), and if not the process is repeated (i.e., step 610). With this process, for example, a machine disinfection algorithm for a dialysis machine can be optimized in conjunction with the process control of the central water processing system to reduce overheating or reheating the inlet water, avoiding undesirable water vaporization or steam. This process also may result in lower usage of the internal heater of the dialysis machine, which can provide energy cost savings for dialysis clinics which use the central water processing system for centralized heat disinfection of dialysis machine inlet lines.

Figure 7:
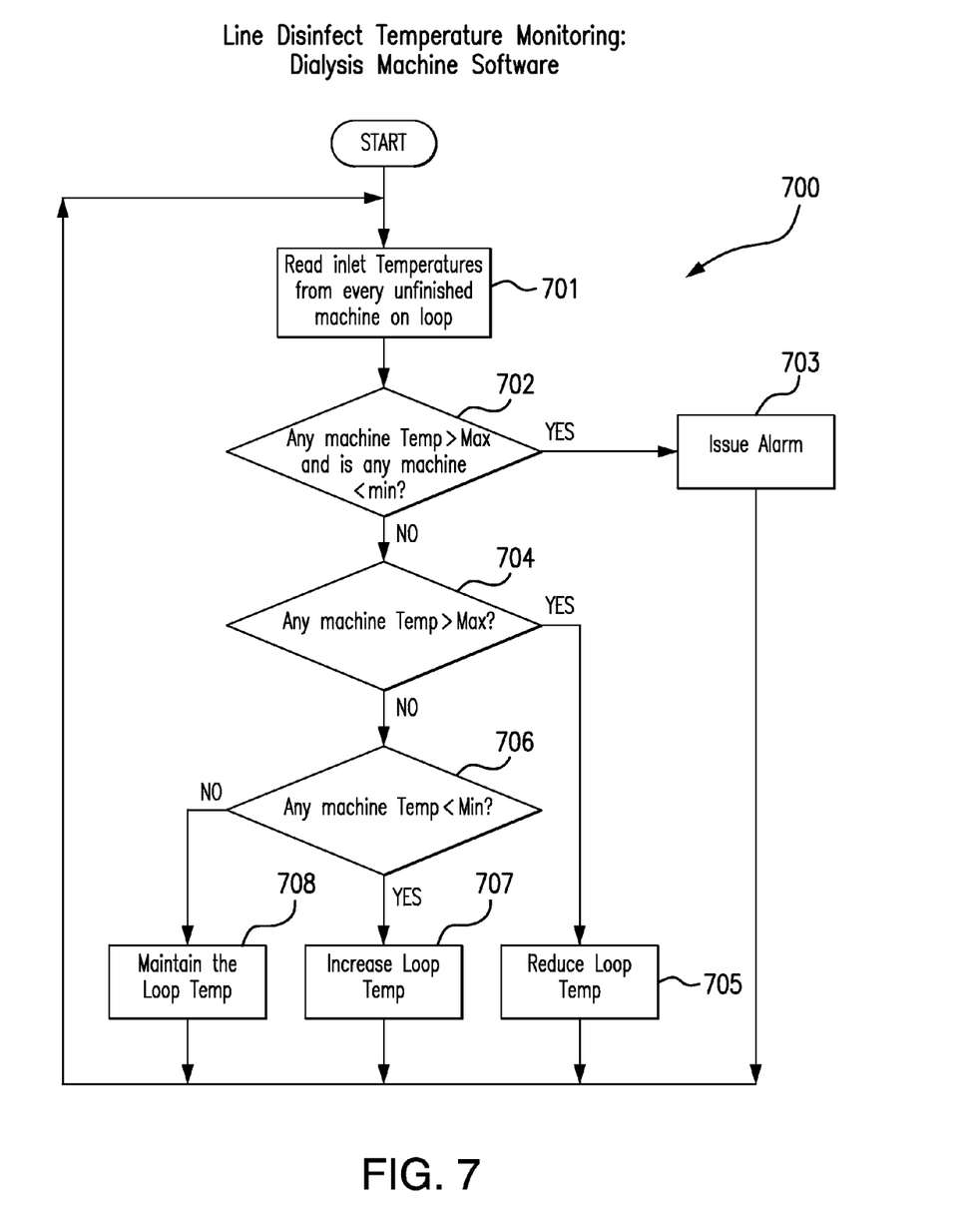
FIG. 7 shows a process flow chart of programming logic of a line disinfect temperature monitoring external process which is integrated with external process controller software, according to an example of the present invention.

As shown in FIG. 7, as an option, a process 700 is shown for line disinfect temperature monitoring which uses external process controller software. In this process, for example, inlet temperatures are read from every unfinished machine on the loop (i.e., step 701). In step 702, the sensed temperature data can be interrogated to see if there is at least one machine that has an inlet temperature above a preselected upper (maximum) temperature range limit (e.g., 99.9° C.) and at least one other machine that has an inlet temperature below a preselected (minimum) temperature range limit (e.g., 85.1° C.). If non-compliant inlet temperatures are identified on multiple machines meeting these criteria, then an alarm can be issued (i.e., step 703) to alert the operator before the process is started over in this instance. If the indicated criteria of step 702 is not met, then the sensed data can be checked to see if at least one machine has an inlet temperature above the preselected upper (maximum) temperature range limit, and if so the loop temperature is reduced in step 705 before the process is restarted, such as manually by an operator or by a command signal transmitted from the external process controller to the temperature controller at the central water processing system. Then, the sensed data is checked to see if at least one machine has an inlet temperature below the preselected lower (minimum) temperature range limit (i.e., step 706), and if so the loop temperature is increased in step 707 before the process is restarted, such as manually by an operator or by a command signal transmitted from the external process controller to the temperature controller at the central water processing system. If no machine inlet temperature is found to be below the preselected lower (minimum) temperature range limit in step 706, the loop temperature is maintained in step 708, and the process is restarted.

As can be appreciated from these various examples, appropriate temperature and flow adjustments at a central water processing system of a dialysis system having centralized heat disinfection of dialysis machine inlet lines can be made without requiring water samples to be drawn and without adding external thermometry to the loop. Other situations, such as tubing variations or flow restrictions which can adversely affect inlet temperature at one or more machines can be detected and addressed with the present systems. Real time or otherwise rapid response adjustments can be made at the central water processing system, for example, to raise the temperature of the water supplied to the loop in a highly controlled manner in response to the lowest non-compliant fluid inlet temperature detected on the loop, while monitoring the effects of the adjustment on the fluid inlet conditions of the non-compliant machine and the other fluid inlets of the other machines on the loop. This also may reduce the occurrence of overcompensating in making temperature and/or flow adjustments in response to a detected non-compliant fluid inlet temperature at a machine. This not only can reduce energy costs, but also can reduce the risk of water vaporization (steam) occurring in the fluid lines. The present method and system also can reduce the need for providing an increased temperature cushion near the beginning of the loop near the outlet of the central water processing system to make sure all fluid inlet lines further downstream on the loop are compliant with a preselected disinfection temperature. The present centralized heat disinfection methods and systems can be applied to dialysis machines in general, including hemodialysis machines, peritoneal dialysis machines, or other types of dialysis machines which require periodic disinfection of an internal hydraulic system.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It will be apparent to those skilled in the art that various modifications and variations can be made to the embodiments of the present invention without departing from the spirit or scope of the present invention. Thus, it is intended that the present invention covers other modifications and variations of this invention provided they come within the scope of the appended claims and their equivalents.

What is claimed is:

1. A method for centralized heat disinfection control for a dialysis system, comprising:
providing a central water processing system, a plurality of dialysis machines having fluid inlets which are fluidly connected to a water supply loop which circulates heated water from the central water processing system to fluid inlets of the dialysis machines and back to the central water processing system;
supplying heated water to the loop from the central water processing system;
sensing water temperature with temperature sensors at the fluid inlets of the plurality of dialysis machines on the loop; and
communicating data on the sensed temperature at the fluid inlets of the dialysis machines to a process controller capable of (i) comparing the sensed temperature to a predetermined value or value range selected for disinfection, and (ii) issuing an alarm or controlling the temperature controller for adjusting water temperature of water at the central water processing system when a sensed inlet water temperature of a dialysis machine does not meet the predetermined value or value range, or both.

2. The method of claim 1, wherein the sensing, communicating, comparing and issuing/controlling steps can be repeated in an iterative manner during the centralized heat disinfection of the fluid inlets.

3. The method of claim 1, wherein the adjusting of the water temperature comprises increasing the water temperature of water at the central water processing system relative to the sensed water temperature at the fluid inlet of the dialysis machine which raised the alarm when a sensed inlet water temperature of a dialysis machine is below the predetermined value or value range.

4. The method of claim 1, further comprising issuing an alarm comprising an audible alarm or an optical alarm, or both, when a sensed inlet water temperature of a dialysis machine is either above or below the predetermined value or value range.

5. The method of claim 1, further comprising conducting of diagnostics on the fluid inlet of a dialysis machine by one of the process controller and temperature controller on the dialysis machine which raised the alarm.

6. The method of claim 1, wherein the predetermined value or value range selected for disinfection is a minimum temperature greater than 85° C.

7. The method of claim 1, wherein the predetermined value or value range selected for disinfection is a temperature of greater than 85° C. and less than 100° C.

8. The method of claim 1, wherein the process controller comprises an automatic programmable controller.

9. The method of claim 1, wherein the temperature controller is controllable by the process controller.

10. The method of claim 1, wherein the temperature controller comprises a manual controller controllable by a human operator.

11. The method of claim 1, wherein the loop comprises at least one subloop having at least one dialysis machine thereon.

12. The method of claim 1, wherein the temperature sensors are located inside housings of the dialysis machines where the fluid inlets make a connection with the machines.

13. The method of claim 1, further comprising integrating the inlet temperature monitoring and process control with a local disinfection program conducted at one or more of the dialysis machines.

14. A dialysis system with centralized heat disinfection control, comprising:
a central water processing system comprising a temperature controller;
a plurality of dialysis machines having fluid inlets which comprise temperature sensors for sensing water temperature;
a fluid supply loop capable of circulating heated water from the central water processing system to the fluid inlets of the plurality of dialysis machines and back to the central water processing system, wherein the at least one temperature sensor senses temperature of fluid supplied from the loop to the fluid inlets; and
a process controller is capable of (a) receiving data on sensed temperatures from the temperature sensors at the fluid inlets of the dialysis machines, (b) comparing the sensed temperatures to a predetermined value or value range selected for disinfection, and (c) issuing an alarm or controlling the temperature controller for adjusting water temperature of water at the central water processing system when a sensed inlet water temperature of a dialysis machine does not meet the predetermined value or value range, or both.

15. The system of claim 14, wherein the dialysis system further is capable of performing the sensing, communicating, comparing and issuing/controlling functions in an iterative manner during a centralized heat disinfection of the dialysis machine inlet lines.

16. The system of claim 14, wherein the process controller comprises a programmable central processing unit (CPU).

17. The system of claim 14, further comprising a wired or wireless communication system providing data transfer between the process controller and the dialysis machines, and control communications between the process controller and the temperature controller of the central water processing system.

18. The system of claim 14, wherein the communication system comprises an ethernet connection.

19. The system of claim 14, wherein the loop comprises at least one subloop having at least one dialysis machine thereon.

20. The system of claim 14, wherein the temperature sensors are located inside housings of the dialysis machines where the fluid inlets make a connection with the machines.

21. The system of claim 14, wherein each dialyzer machine further comprises a functional processor board in bidirectional communication with the process controller.

22. The system of claim 14, wherein central water processing system further comprises a pump unit for moving the heated water through the loop.

23. The system of claim 14, further comprising an integration of the inlet temperature monitoring and process control with a local disinfection or heater program conducted at one or more of the dialysis machines.

* * * * *